United States Patent [19]

Pekkarinen

[11] Patent Number: 4,526,574
[45] Date of Patent: Jul. 2, 1985

[54] DIFFERENTIAL OCCLUSION SENSING METHOD AND APPARATUS

[75] Inventor: Michael O. Pekkarinen, Lincolnshire, Ill.

[73] Assignee: Baxter Travenol Laboratories, Inc., Deerfield, Ill.

[21] Appl. No.: 497,369

[22] Filed: May 23, 1983

[51] Int. Cl.³ .............................................. A61M 5/00
[52] U.S. Cl. ...................................... 604/52; 604/65; 604/118; 128/DIG. 13
[58] Field of Search .................. 604/31, 53, 65, 67, 604/245, 246, 49, 118; 128/DIG. 13, DIG. 3; 340/611, 614, 626; 73/119 A, 730

[56] References Cited
U.S. PATENT DOCUMENTS

| Re. 31,315 | 7/1983 | Jenkins et al. ........................ 604/67 |
| 4,210,138 | 7/1980 | Jess et al. . |
| 4,213,454 | 7/1980 | Shim . |
| 4,217,993 | 8/1980 | Jess et al. . |
| 4,299,218 | 11/1981 | Knigge et al. . |
| 4,373,525 | 2/1983 | Kobayashi . |
| 4,385,630 | 5/1983 | Gilcher et al. ........................ 604/67 |
| 4,394,862 | 7/1983 | Shim ...................................... 604/67 |
| 4,431,425 | 2/1984 | Thompson et al. ................... 604/65 |

Primary Examiner—John D. Yasko
Assistant Examiner—Michelle N. Lester
Attorney, Agent, or Firm—Robert A. Benziger; Paul C. Flattery

[57] ABSTRACT

The present invention provides an accurate method and apparatus for sensing and monitoring any buildup in the downline tubing pressure in a fluid infusion system. The initial fluid pressure as indicated by the tubing location is sensed after a delay period and is utilized as a base pressure if it is within allowable limits. The infusion tubing location or pressure is then monitored and compared with the base location or pressure. The system will alarm if a preset differential location or pressure change is exceeded.

15 Claims, 2 Drawing Figures

DIFFERENTIAL OCCLUSION SENSING METHOD AND APPARATUS

BACKGROUND OF THE INVENTION

The present invention relates generally to fluid infusion systems and more particularly is directed to a method and apparatus for accurately detecting small changes in tubing dimensions to prevent high pressure infusion into the fluid infusion system.

The infusion of fluids into the human body is usually accomplished by means of an administration set in conjunction with metering apparatus which controls the rate of flow of fluid through the set. Peristaltic-type pumps, which function by repetitively compressing and expanding a section of tubing, have proven particularly attractive for use in metering apparatus since they do not introduce the possibility of leakage or contamination into the system, while providing positive control fo fluid flow through the system.

One form of peristaltic-type pump which is particularly well adapted for infusion applications is described in U.S. Pat. No. 4,155,362. Basically, this pump construction includes individually spring-biased rollers in the pump rotor which provide a uniform compression force, and a spring-biased plunger which restricts the lumen of the administration set downline of the pump rotor to provide a back pressure against which the pump must work. This prevents the release of dissolved gas in the tubing section, assists in restoring the tubing to its original shape following compression by the pump, and prevents uncontrolled gravity flow in the event of pump failure.

A potential problem with this and other types of infusion systems relates to detecting pressure increases downline of the pump or pump restrictor in order to avoid patient harm which may occur as a consequence of excessive fluid pressure. Some prior systems have included sensing means with the pumping system, but these are ineffective downline of pumping systems which are isolated from downline pressure variations by some type of restrictor.

One prior attempt at solving this problem was the use of a push rod microswitch system. As the tubing would swell from the increase in pressure caused by an occlusion downline of the pump, the rod would activate the microswitch and cause an alarm and/or stop the pump. A basic problem with this type of microswitch system is that the calibration of the system requires that the switch respond at a specific position. Therefore, anything which affects the alignment and contact pressure between the push rod and the tubing has the capability of changing significantly the internal pressure which is required to cause the tubing to swell sufficiently in order to trigger the microswitch. Further, the stability of the mechanical system and the microswitch has to be accurate enough to measure as little as 0.001 inch travel. Variations such as spring fatigue and friction variations introduce other deviations in the operation. The cross sectional shape that the tubing has at the time of insertion into the pump can vary from circular to extremely elliptical. This can result in differences as large as two to one in the dimension which is sensed by the push rod.

Further, the tubing itself will vary in wall thickness and inside diameter by about 0.01 inch. In addition the tubing material itself will vary in the pressure it takes for it to swell a certain amount. The operating temperature range and age of the tubing will cause variations in the amount of swelling per unit of pressure. These many variations can cause the actual pressure at which the push rod system will alarm to vary widely from infusion set to infusion set and with each insertion of the same tubing into the pump.

SUMMARY OF THE INVENTION

In accordance with the present invention, a method and apparatus is provided to sense the downline pressure variations in the infusion tubing of a fluid infusion system on a differential basis. The invention allows for normal operation of the infusion system while monitoring any change in the tubing, swelling, and hence the internal pressure from the moment of pump initiation.

Thus, the initial location of the tubing is sensed a set time period after initiation of the infusion. The initial sensed location value is compared against a predetermined allowable range and is stored if it is within that range. The initial value thus takes all present factors into accord and is utilized as the base value. If the pressure changes by a preset differential amount from the base value amount as determined by sensing the change in the tubing location, the system will alarm.

DESCRIPTION OF THE PREFERRED EMBODIMENT

Figure 1:
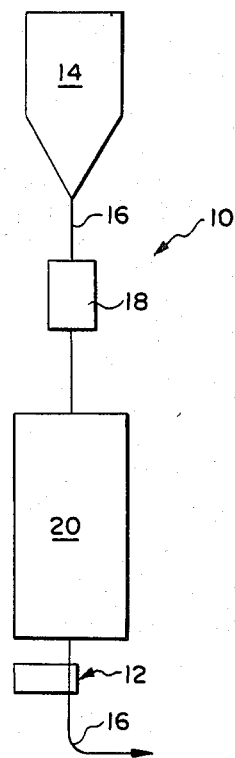
FIG. 1 is a schematic diagram of an infusion system.

Referring to FIG. 1, there is shown diagrammatically an infusion system 10, which can incorporate the present invention of a differential pressure sensing system 12. A fluid to be infused or injected into a vein or artery is contained in a fluid source or reservoir 14. The fluid is coupled through a standard fluid set which includes a flexible, collapsible tubing 16, which can be in one or more segments as desired.

The tubing 16 couples the fluid through a drip chamber 18 and into a pump assembly 20. Although a peristaltic pump assembly 20 is preferred, and hereinafter described, the invention is not limited to any particular type of pumping system. After passing through the pump 20, the tubing is coupled through the pressure sensor 12 and then to the vein or artery (not shown) into which the fluid is to be infused. Although the sensor 12 is illustrated as a separate unit downline of the pump 20, it preferably can be part of the pumping assembly rather than a separate unit. However, the sensor 12 operates independently of the particular pumping system, which is at least partially isolated, as by a restrictor, from the downstream pressure changes to be monitored.

Figure 2:
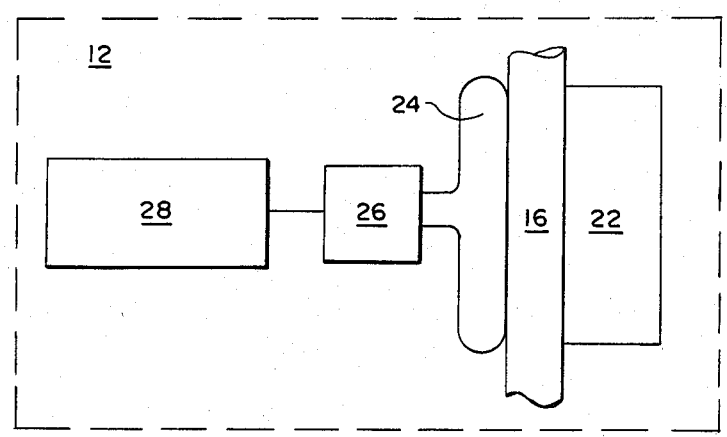
FIG. 2 is a schematic diagram of a differential pressure sensor of the present invention.

Referring to FIG. 2, the pressure sensor 12 is best illustrated. The sensor 12 includes a fixed block 22, against which the tubing 16 is pressed by a location indicator transmitter 24. The indicator 24 can be pneumatic, hydraulic or electronic, but functions to transmit the location or swelling of the tubing 16 to a transducer 26. The transducer 26 transmits a signal indicating the sensed location to a controller 28, such as a microprocessor. The controller 28 converts the location of the indicator 24 to a value indicative of the pressure in the tubing 16. The transmitter 24 and transducer 26 can be separate units as shown, or can be one integral unit.

In operation, the pump 20 is activated causing an initial operating pressure to be developed, which may cause the tubing 16 to swell. The tubing position due to the tubing configuration or caused by the swelling is sensed by the indicator 24 and transducer 26 which transmits a signal to the controller 28. The controller 28 converts the position sensed to a pressure and compares the initial pressure value to an allowable pressure range, such as up to 20 psi. If the initial pressure value is within the allowable range, the value is stored and if it is outside the range, the controller 28 will cause the system 10 to alarm.

The controller 28 then utilizes the base location as the standard location to monitor the infusion process. If the location and hence the pressure varies at any time beyond a predetermined differential amount from the base pressure, such as 5 psi, then the system will alarm. The alarm limit can include a predetermined change in pressure from the base pressure and can include a maximum operating pressure for the system, such as 25 psi.

Thus, an initial base location and hence pressure is obtained which eliminates variations in the tubing position, thickness, diameter and shape. In a hydraulic system the transmitter 24 will be formed from a flexible material such as silicone and will contain an incompressible fluid to transmit the location in the form of pressure to the transducer 26.

Modifications and variations of the present invention are possible in light of the above teachings. The controller 28 preferably converts the sensed location to pressure which then can be displayed for operator use; however, the controller also can operate directly on location changes without conversion. It is therefore to be understood that within the scope of the appended claims the invention may be practiced, otherwise than as specifically described.

What is claimed and desired to be secured by Letters Patent of the United States is:

1. A method of sensing and monitoring downline fluid pressure in a fluid infusion system, comprising:
   providing a fluid tubing;
   providing a positive fluid flow in said tubing;
   sensing an initial base operating location of a single portion of said tubing;
   monitoring the tubing portion location;
   comparing the monitored location against the initial base operating location; and
   setting an alarm if said monitored location exceeds a predetermined location differential.

2. The method as defined in claim 1 including:
   sensing said initial base operating location after a predetermined time delay.

3. The method as defined in claim 1 including:
   providing an absolute alarm location;
   comparing the monitored location against the absolute alarm location; and
   setting an alarm if said monitored location exceeds said absolute alarm location.

4. The method as defined in claim 1 including:
   providing an allowable initial location range;
   comparing said initial base operating location against said allowable initial location range; and
   setting an alarm if said initial base operating location is outside of said allowable initial location range.

5. The method as defined in claim 1 including:
   converting said initial base operating location and said monitored location to values indicative of the internal tubing pressure and representing an initial base pressure and a monitored pressure; and
   setting said alarm if said monitored pressure exceeds a predetermined pressure differential.

6. The method as defined in claim 5 including:
   sensing an initial infusion operating pressure after a predetermined time delay;
   providing an allowable initial pressure range;
   comparing said initial infusion operating pressure against said allowable initial pressure range; and
   setting an alarm if said initial infusion operating pressure is outside of said allowable initial pressure range.

7. The method as defined in claim 6 including:
   providing an absolute alarm pressure;
   comparing the monitored pressure against the absolute alarm pressure; and
   setting an alarm if said monitored pressure exceeds said absolute alarm pressure.

8. An apparatus for sensing and monitoring downline fluid pressure in the fluid tubing of a fluid infusion system, comprising:
   means adapted to be coupled to the fluid tubing for sensing the location of a single portion thereof;
   means coupled to said sensing means for monitoring said sensed portion location and comparing it to an initial sensed infusion operating location; and
   means for setting an alarm if said sensed portion location exceeds a predetermined location differential.

9. The apparatus as defined in claim 8 including:
   delay means for sensing said initial infusion operating location after a predetermined time delay.

10. The apparatus as defined in claim 8 including:
    means for comparing the monitored location against an absolute alarm location; and
    means for setting an alarm if said monitored location exceeds said absolute alarm location.

11. The apparatus as defined in claim 8 including:
    means for comparing said initial infusion operating location against a predetermined allowable initial location range; and
    means for setting an alarm if said initial infusion operating location is outside of said predetermined allowable initial location range.

12. The apparatus as defined in claim 8 wherein:
    said location sensing means include a fluid transducer adapted to be fluidly coupled to the tubing.

13. The apparatus as defined in claim 8 including:
    means for converting said sensed portion location and said monitored location to values indicative of the internal tubing pressure and representing an initial infusion operating pressure and a monitored pressure; and
    means for setting said alarm if said monitored pressure exceeds a predetermined pressure differential.

14. The apparatus as defined in claim 13 including:
    delay means for sensing said initial infusion operating pressure after a predetermined time delay;
    means for comparing said initial infusion operating pressure against an allowable initial pressure range; and
    means for setting an alarm if said initial infusion operating pressure is outside of said allowable initial pressure range.

15. The apparatus as defined in claim 14 including:
    means for comparing the monitored pressure against an absolute alarm pressure; and
    means for setting an alarm if said monitored pressure exceeds said absolute alarm pressure.

* * * * *